United States Patent [19]

Shkidchenko et al.

[11] 4,379,846
[45] Apr. 12, 1983

[54] FERMENTATION APPARATUS

[76] Inventors: Alexandr N. Shkidchenko, Puschino, mikroraion "G", 30, kv. 51; Boris F. Nesterov, Puschino, mikroraion "V", 24, kv. 62; Vyacheslav G. Sharov, Puschino, mikroraion "V", 22, kv. 45; Boris I. Smolin, Puschino, 25, kv. 5, all of Moskovskaya oblast, U.S.S.R.

[21] Appl. No.: 257,598

[22] Filed: Apr. 27, 1981

[51] Int. Cl.³ .................... C12M 1/02; C12M 1/06; C12M 1/14

[52] U.S. Cl. .................................. 435/316; 435/310; 435/315

[58] Field of Search .................. 435/315, 316, 310

[56] References Cited

U.S. PATENT DOCUMENTS

| | | | |
|---|---|---|---|
| 3,407,120 | 10/1968 | Weiss et al. | 195/104 |
| 3,701,713 | 10/1972 | Bennett et al. | 435/316 X |
| 3,801,468 | 4/1974 | Lumb et al. | 195/141 |
| 3,843,454 | 10/1974 | Weiss | 195/127 |
| 3,925,165 | 12/1975 | Muller | 195/127 |
| 4,286,065 | 8/1981 | Kaluniants et al. | 435/316 X |

FOREIGN PATENT DOCUMENTS 579302  11/1977  U.S.S.R.

Primary Examiner—Robert J. Warden
Attorney, Agent, or Firm—Fleit, Jacobson & Cohn

[57] ABSTRACT

A fermentation apparatus for use with liquid substrates comprises a housing having arranged therein a shaft of an agitation means provided with stirrers. Arranged in the interior of the housing are two groups of elements intended for the cultivation of layers of microorganisms thereon, the elements acting to expand the useful interior area of the apparatus, the two groups being adapted to form a gap therebetween. At least one group of the elements is adapted to be moved relative to another group to thereby control the thickness of the layer of the microorganisms being cultivated in said gap during the movement.

7 Claims, 4 Drawing Figures

FERMENTATION APPARATUS

FIELD OF THE INVENTION

The present invention relates to devices for the cultivation of microorganisms, and more particularly to fermentation apparatus for use with liquid nutrient media or substrates.

The invention can find application in microbiology, medicine, food industry and research practice, especially for the cultivation of the mycelium forms of microorganisms.

BACKGROUND OF THE INVENTION

Microorganisms are usually cultivated in apparatuses provided with agitation means or stirrers to ensure that the fermentable liquid is uniformly mixed throughout the entire inner volume of the apparatus. When growing microorganisms tending to produce filamentous mycelium, no prior art apparatus can assure uniform distribution of the living cells because the walls and the stirrer thereof become grown with clots of mycelium. Some mycelium clots float freely in the fermentation liquid and therefore are subject to mechanical destruction during stirring.

The supply of nutrient media to the mycelium being cultivated in the heretofore described conditions and the withdrawal of a metabolic product from the apparatus become too complicated, while some mycelium in the newly formed clots tend to die. This in turn results in that the growth of mycelium microorganisms tends to become uncontrollable, therefore rendering practically impossible the continuous cultivation of the mycelium forms of microorganisms. Accordingly, the principle whereby microorganisms are distributed uniformly throughout the fermentation liquid cannot be adopted in the case of cultivating mycelium microorganisms.

Known in the art is an apparatus for cultivating tissue cells of a horizontal type comprising a housing partially filled with liquid nutrient media, the housing also accommodating a shaft of an agitation means provided with disk elements serving as carrying surfaces for the tissue cells (cf. USSR Inventor's Certificate No. 579,302 Cl. C 12 b 1/10).

The above apparatus is not provided with means for controlling the thickness of the layer of living cells growing on the surfaces of the disk elements, the cells thereby tending to fill the gaps between the disk elements. The apparatus needs to be disassembled in order to evacuate the cells from the gaps.

Mass transfer of the cells with the fermentation liquid is effected by immersing the disks into the substrate, which makes it impossible to carry out a continuous flow-through of the substrate to feed the cells.

Also known is a fermentation apparatus comprising a housing filled with fermentable liquid and accommodating a shaft of an agitation with stirrers (cf., e.g., U.S. Pat. No. 3,801,468, Cl. 195-141, published 1974).

The above apparatus is further provided with ribs or baffles secured to the inner wall of the apparatus and serving to guide the flow of the fermentable liquid.

Cultivation of microorganisms in the apparatus is accompanied by the formation of growths of living cells on the interior surfaces. However, the thickness of the layer of cells is non-uniform and cannot be effectively controlled. Further, the layer cannot be effectively fed with the nutrient media, while some of the cells inside the layer are liable to die, thus rendering a continuous controllable cultivation impossible.

SUMMARY OF THE INVENTION

It is therefore an object of the present invention to provide a fermentation apparatus for use with liquid substrates which would afford to effectively control the rate of growth of the microorganisms to produce biologically active substances in the course of a continuous cultivation.

The object is attained in a fermentation apparatus for use with liquid substrates comprising a housing having arranged therein a shaft of an agitation means provided with stirrers, in which apparatus, according to the invention, there are provided in the interior of the housing two groups of elements intended for the cultivation of layers of microorganisms thereon, the elements acting to expand the useful interior surface of the apparatus and adapted to form a gap therebetween, while at least one group of the elements is adapted to move relative to another group so as to control during the movement the thickness of the layer of microorganisms being cultivated in said layer.

In order to produce a layer of microorganisms of a preset thickness, one group of the elements intended for the cultivation of microorganisms thereon are preferably shaped as disks secured to the shaft of the agitation means and serving as stirrers thereof, while another group of the elements intended for the cultivation of microorganisms thereon are preferably fashioned as annular projections or baffles secured to the inner surface of the housing and interposed essentially between the disks.

For a more efficient supply of the substrate to the microorganisms being cultivated the shaft of the agitation means and the disks thereof, the inner walls of the housing and the annular baffles are preferably hollow to communicate therebetween, fabricated from a capillary porous material and filled with the liquid substrate.

Alternatively, one group of the elements intended for the cultivation of microorganisms thereon may have the form of coaxially disposed cylinders secured to a main shaft of the agitation means and serving as main stirrers thereof, whereas another group of the elements intended for the cultivation of microorganisms thereon may likewise have the form of coaxially arranged cylinders secured to a secondary shaft of the agitation means, the shaft being disposed coaxially relative to the main shaft for rotation in a direction opposite to the direction of rotation of the main shaft, the lastmentioned cylinders being interposed between the cylinders of the main shaft and serving as secondary stirrers of the agitation means.

In order to provide for unobtrusive circulation of the substrate, the cylinders are preferably of meshed construction.

Preferably, the cylinders are attached to the main and secondary shafts of the agitation means by way of separate disks, the inside of the disks being provided with passageways for feeding the liquid substrate to the interior of the apparatus and for evacuating the spent substrate therefrom; the main shaft is preferably hollow to communicate with the passages for the supply of the liquid substrate.

The heretofore described arrangement of a fermentation apparatus according to the invention provides for a continuous controllable cultivation of microorganisms.

BRIEF DESCRIPTION OF THE DRAWINGS

These and other objects of the present invention will become more fully apparent by referring to specific embodiments thereof taken in conjunction with the accompanying drawings, in which.

The fermentation apparatus according to the invention will be disclosed hereinafter as an apparatus specifically intended for the cultivation of mycelium forms of microorganisms.

DETAILED DESCRIPTION OF THE INVENTION

Figure 1:
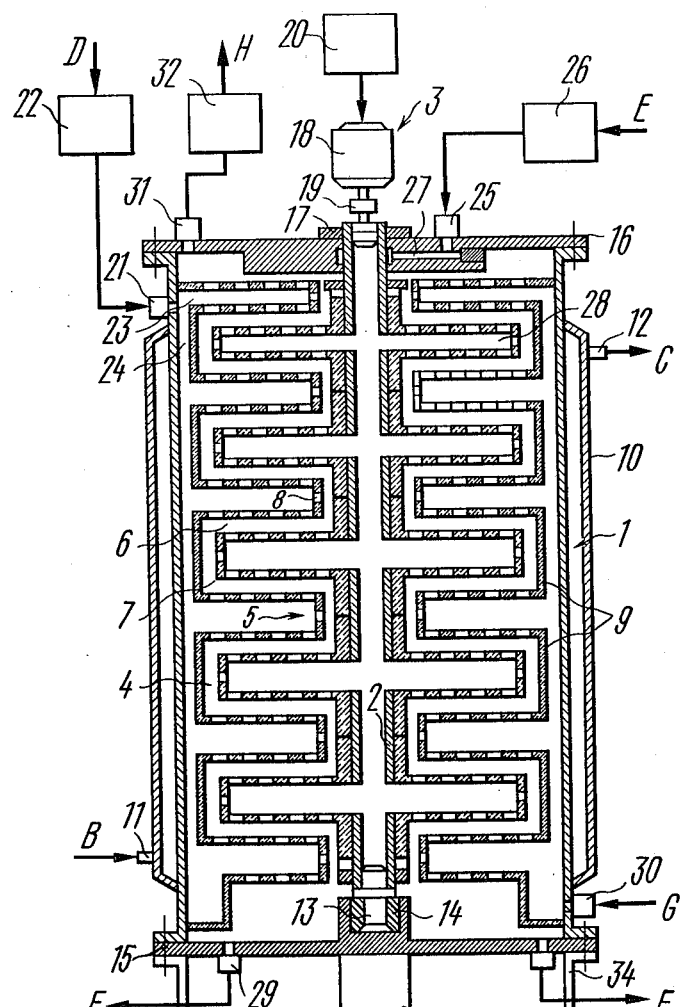
FIG. 1 is a longitudinal section of a fermentation apparatus according to the invention.

With reference to FIG. 1, there is shown an apparatus according to the invention comprised of a housing 1 to be filled with liquid substrate or nutrient media. Disposed inside the housing 1 are a shaft 2 of an agitation means or stirrer 3 and two groups of elements 4 and 5 intended for a layer of mycelium microorganisms to grow thereon.

The two groups of the elements 4 and 5 act to expand the inner surface area of the apparatus, the groups being spaced from one another to form a gap 6 therebetween.

The group of elements 4 is adapted to rotate relative the group of elements 5 so as to control the thickness of the layer of microorganisms being grown in the gap 6.

In the herein described embodiment of the apparatus, the group of elements 4 intended for the growth of living cells being fermented represent generally disks 7 affixed to the shaft 2 of the agitation means 3, the disks 7 serving as stirrers thereof, whereas another group of the elements 5 are shaped as annular projections or baffles 8 made integral with inner walls 9 of the housing 1 of the apparatus, the baffles being interposed between the disks 7.

The shaft 2 of the agitation means 3, the disks 7 thereof, as well as the walls 9 of the housing 1 and the baffles 8 thereof are hollow to be capable to communicate therebetween, fabricated from a capillary porous material (except the outer wall 9) and filled with a liquid nutrient media.

Compressed glass crumb is used as the above porous material. Alternatively, compressed metal crumb may be used for the same purpose.

The apparatus further comprises a temperature-controlled jacket 10 enclosing the housing 1 and provided with inlet and outlet means 11 and 12 respectively for the supply in the direction of the arrow B of a cooling agent and the withdrawal thereof along the path indicated by the arrow C.

The shaft 2 of the stirrer 3 is rotatably secured in a bearing 13 in turn journaled in a sleeve 14, the sleeve 14 being fixed in a bottom lid 15 of the housing 1. A top lid 16 of the housing 1 accommodates another end of the shaft 2 by means of a sleeve 17, the shaft being further connected to an output shaft of a power means or motor 18 of the stirrer 3 through a coupling 19, the motor 18 being electrically wired to a control unit 20.

Installed in the outer wall 9 is a pipe 21 intended for the supply of the liquid nutrient media or substrate in the direction generally indicated by the arrow D from a metering pump 22 into cavities 23 of the baffles 8 and further into a cavity 24 formed between the inner and outer walls 9 of the housing 1 and then through the capillaries of the porous material into the gap 6 between the disks 7 and baffles 8.

Provided in the top lid 16 is an inlet pipe 25 for the supply of the liquid nutrient media in the direction generally indicated by the arrow E from a metering pump 26 along a passageway 27 provided in the lid 16 into hollow 28 of the shaft 2 and further via the capillary porous material into the gap 6 between the disks 7 and baffles 8.

The bottom plate 15 accommodates two pipes 29 for the evacuation of the worked out or spent substrate, the direction of the evacuation being indicated generally by the arrows F.

The outer wall 9 and the top plate 16 of the housing 1 are provided with pipes 30 and 31 respectively for the supply along the path indicated generally by the arrow G and discharge along the arrow H of air. The air escaping the apparatus through the pipe 31 is caused to pass through a filter means 32 and only then is discharged into the atmosphere.

The outer surface of the bottom plate 15 comprises support brackets 33 and 34.

The heretofore described modification of the apparatus according to the invention can be used with advantage for fermentation on mycelium microorganisms, such as those produced during the manufacture of antibiotics.

Figure 2:
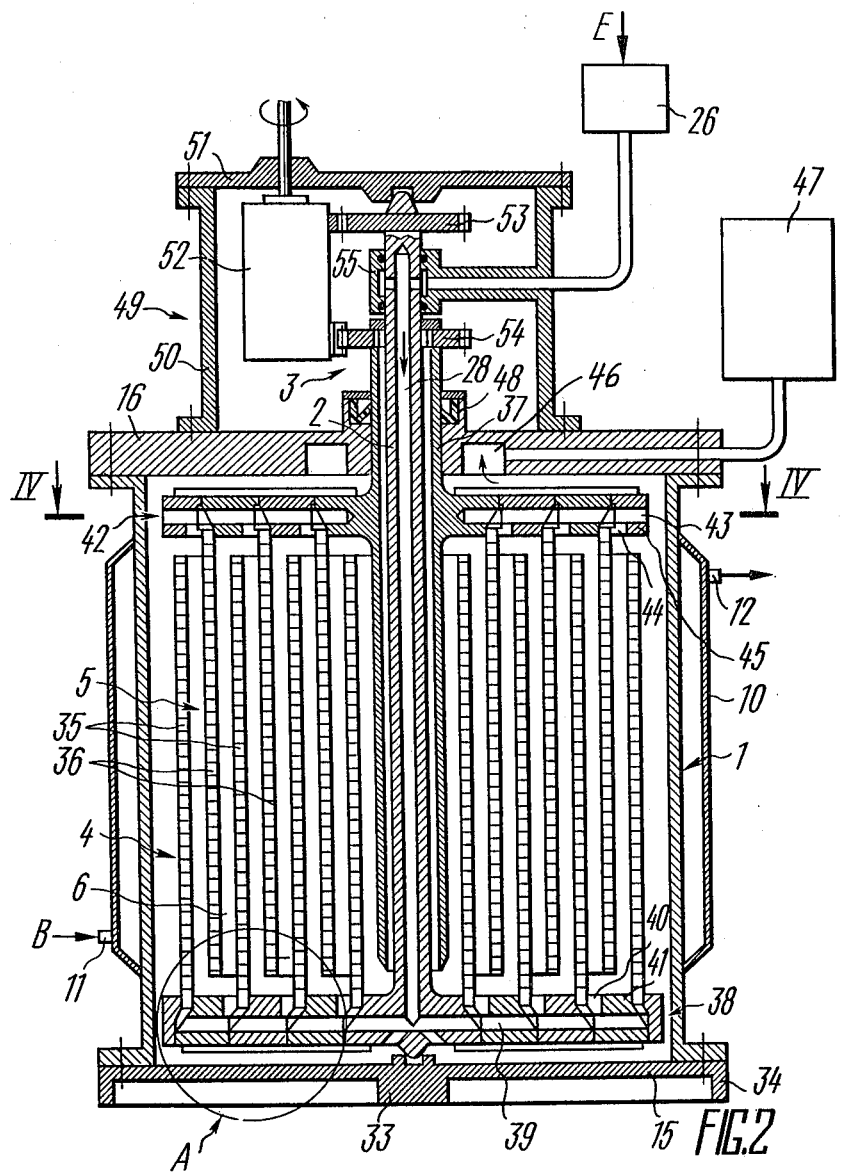
FIG. 2 is another modified form of the fermentation apparatus according to the invention, a longitudinal section.

Another modified form of the apparatus according to the invention as represented in FIG. 2 is preferably used for the growth of monocelled microorganisms.

With reference to the above Figure, the two groups of elements 4 and 5 intended to bear the microorganisms being grown thereon are arranged to move or rotate relative one another to thereby control the thickness of the layers of microorganisms in the gap 6 formed therebetween. To this end, one group of the elements 4 is fashioned as coaxially positioned cylinders 35; the cylinders are affixed to one shaft 2 and also serve as stirrers. Another group of elements 5 is likewise intended for microorganisms to grow thereon and also have the form of coaxially arranged cylinders 36 secured to another shaft 37 of the agitation means 3. The shaft 37 is coaxial with the shaft 2 and capable of rotating in a direction opposite to the direction of rotation of the shaft 2. The cylinders 36 interposed between the cylinders 35 serve as additional stirrers of the agitation means 3.

The cylinders 35 and 36 are preferably multi-perforated or meshed.

Figure 3:
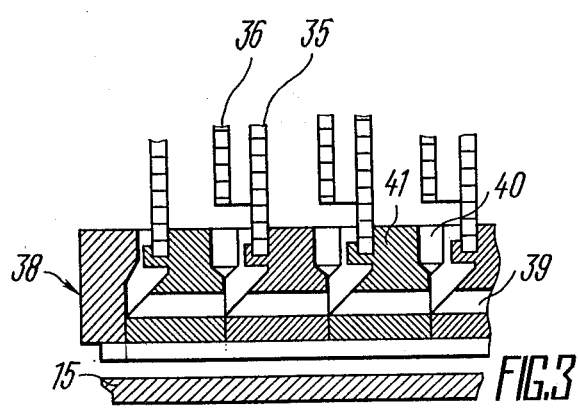
FIG. 3 is an enlarged view of the section A in FIG. 2.

The cylinders 35 are spaced from one another and fixedly secured to a separate disk member 38, the interior of the disk member being provided with passageways 39 (FIG. 3) for the supply of the liquid substrate into the apparatus, the passageways communicating with the hollow or cavity 28 of the shaft 2 (FIG. 2) and with the interior of the apparatus via openings 40 provided in the disk member 38. The disk member 38 (FIG. 3) is made up of ring elements 41, the hollow 28 of the shaft 2 (FIG. 2) communicating with the metering pump 26.

Figure 4:
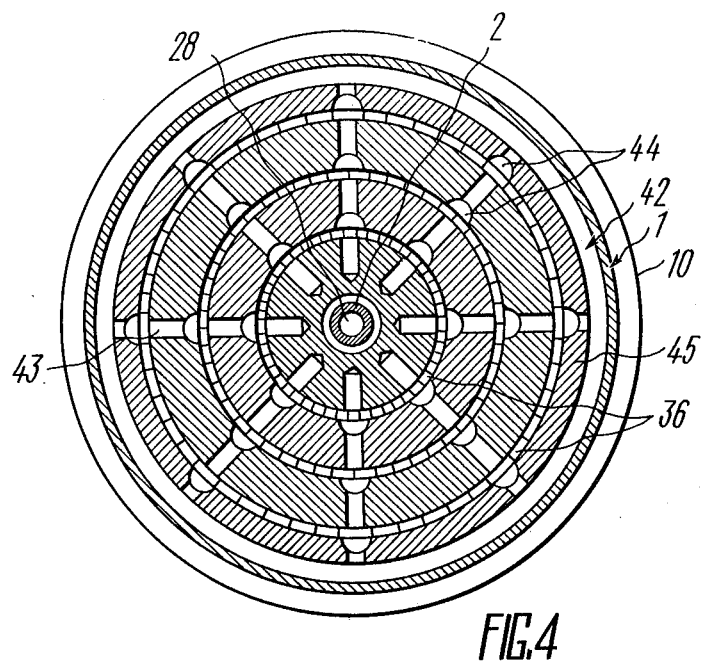
FIG. 4 is a section taken on the line IV—IV of FIG. 2.

The cylinders 36 are connected with the shaft 37 of the agitation means 3 by means of a separate disk member 42, the interior of which is provided with passageways 43 (FIG. 4), said passageways serving to evacuate the worked out or spent substrate from the interior of the apparatus through openings 44 provided in the disk member 42. The disk member 42 is made up of ring elements 45.

The spent substrate is caused to flow into a passageway 46 (FIG. 2) provided in the top plate of the housing 1 to enter a collector 47.

The shaft 37 is provided with a packing ring 48 secured in the top plate 16.

Attached to the top plate 16 is a drive means for the shafts 2 and 37 indicated generally by the numeral 49 and comprised of a housing 50 having a top lid 51 and a reducer 52 affixed to the top lid 51 and kinematically linked with the shafts 2 and 37 by means of gear transmissions 53 and 54, respectively.

The shaft 2 is pressure-sealed by means of a sealing element 55.

The operating principle of the fermentation apparatus according to the invention resides in the following.

The apparatus is filled with a liquid nutrient media through the pipes 21 and 25 (FIG. 1) followed by the introduction of initial cells of microorganisms via the pipe 25. With a preset temperature being maintained inside the apparatus, the nutrient media containing the living cells is then stirred by rotating the shaft 2 carrying the disks 7. The nutrient media or substrate is aerated by a flow of air introduced into the cavities 23 and 24 through the pipe 30. The air and substrate are then forced into the gap 6 via the inner wall 9 and baffles 8 and via the shaft 2 and disks 7.

In the course of their growth, the microorganisms tend to adhere to the surface of the inner wall 9 of the housing 1 and to the baffles 8, as well as to the surfaces of the shaft 2 and disks 7.

The thickness of the layer of the thus cultivated microorganisms is limited by the value of the gap 6 defined between the baffles 8 of the inner wall 9 and the disks 7 of the shaft 2 of the agitation means 3. Excessive growth of the living cells is removed mechanically by rotating the disks 7, and further by entrainment in the stream of spent substrate via the pipe 29. The discharge air is evacuated through the pipe 31 and filter 32.

Fresh substrate is supplied through the pipes 21 and 25 by the metering pumps 22 and 26, respectively.

The microorganisms are caused to grow on the thus enlarged interior area of the apparatus, while necrosis of the cultivated microorganisms fails to occur thanks to a constant influx of fresh substrate and air. The apparatus is preferably filled to the full with the nutrient media.

The operating principle of the modification of FIG. 2 is substantially similar to that of the embodiment shown with reference to FIG. 1. The difference is in as follows.

The apparatus is likewise filled with a substrate fed through the metering pump 26 (FIG. 2), hollow 28 of the shaft 2 and the passageways 39 (FIG. 3) of the disk 38. The liquid substrate is thereby caused to enter the interior of the apparatus via the openings 40 of the disks 38, air being supplied in a much the same manner.

Living cells of microorganisms are then introduced, whereafter the substrate is stirred by causing the shafts 2 (FIG. 2) and 37 to rotate in the opposite directions, the shafts carrying the meshed cylinders 35 and 36, respectively. The fermented substrate tends to form a layer of living cells on the meshed surface of the cylinders 35 and 36, the thickness of this layer being restricted by the value of the gap 6 between said cylinders. Excessive growth is removed mechanically by the rotating cylinders 35 and 36 and evacuated from the apparatus by entrainment in the stream of spent substrate via the passageways 43 (FIG. 4) and openings 44 of the disk 42 and via the passageway 46 (FIG. 2) to be collected in the collector 47. The used air is discharged in a similar manner.

Microorganisms tend to grow on the entire surface of the meshed cylinders 35 and 36. The apparatus is preferably filled to the full with the nutrient media.

Having in view the foregoing, the fermentation apparatus according to the invention provides continuous cultivation of microorganisms, especially mycelium microorganisms, which hithertofore were cultivated by batch methods. This makes the process of microbial synthesis controllable, which is especially important in the production of biologically active substances. The governable conditions for cultivating mycelium forms of microorganisms make it possible to pave the way to a purpose-oriented increase in the productivity of microorganisms.

The fermentation apparatus according to the invention can find application for immobilization of living cells when fermented by nonspecialized substrates.

What is claimed is:

1. A fermentation apparatus for use with liquid substrates comprising:
    a temperature-controlled jacket;
    a housing defined by walls having an inner surface, the housing being disposed inside said temperature-controlled jacket and adapted to be filled with said liquid substrate;
    an agitation means having a shaft with stirrers accommodated in the interior of said housing, the shaft of the agitating means and the walls of said housing being made hollow and being made from a capillary-porous material;
    a first group of elements intended for the cultivation of a layer of microorganisms thereon disposed inside said housing and acting to expand the useful interior surface of the apparatus;
    a second group of elements intended for the cultivation of a layer of microorganisms thereon disposed inside said housing and acting to expand the useful interior surface of the apparatus;
    a gap formed between said groups of elements; and
    at least one said group of elements arranged to be capable of movement relative to another said group of elements such that during the movement the elements of this group act to control the thickness of said layer of microorganisms being cultivated in said gap.

2. The apparatus of claim 1 wherein
    the first group of elements intended for the cultivation of a layer of microorganisms thereon have the form of disks secured to the first shaft of said agitation means to serve as first stirrers thereof; and
    the second group of elements intended for the cultivation of a layer of microorganisms thereon have the form of annular projections or baffles made integral with said inner surface of said walls of said housing, the baffles being interposed between said disks.

3. An apparatus of claim 2 wherein the first shaft of said agitation means, said walls of said housing and said annular baffles are hollow to communicate therebetween and made from a capillary porous material and filled with said liquid substrate.

4. An apparatus of claim 1 wherein said agitation means has a second shaft provided with second stirrers, the shaft being arranged inside the housing coaxially relative to the first shaft for rotation in a direction opposite to the direction of rotation of the first shaft;

the first group of elements intended for the cultivation of a layer of microorganisms thereon are shaped as coaxially disposed first cylinders connected to the first shaft of said agitation means and serving as first stirrers thereof; and the second group of elements intended for the cultivation of a layer of microorganisms are also shaped as coaxially disposed second cylinders connected to a second shaft of said agitation means interposed between the first cylinders and serving as second stirrers of said agitation means.

5. An apparatus of claim 4 wherein said cylinders have meshed structure.

6. An apparatus of claim 4 further comprising
a first disk secured to the first shaft of said agitation means, the disk being adapted to carry the first cylinders;
passageways for the supply of said liquid substrate to the interior of the apparatus provided inside the first disk and adapted to communicate with the hollow of the first shaft;
a second disk secured to the second shaft of said agitation means, the disk being adapted to carry the second cylinders; and
passageways for the withdrawal of said liquid substrate from the interior of the apparatus, the passageways being provided inside the second disk.

7. An apparatus of claim 5 further comprising
a first disk secured to the first shaft of said agitation means, the disks being adapted to carry the first cylinders;
passageways for the supply of said liquid substrate to the interior of the apparatus provided inside the first disk and adapted to communicate with the hollow of the first shaft;
a second disk secured to the second shaft of said agitation means, the disk being adapted to carry the second cylinders; and
passageways for the withdrawal of said liquid substrate from the interior of the apparatus, the passageways being provided inside the second disk.

* * * * *